Figure 5:
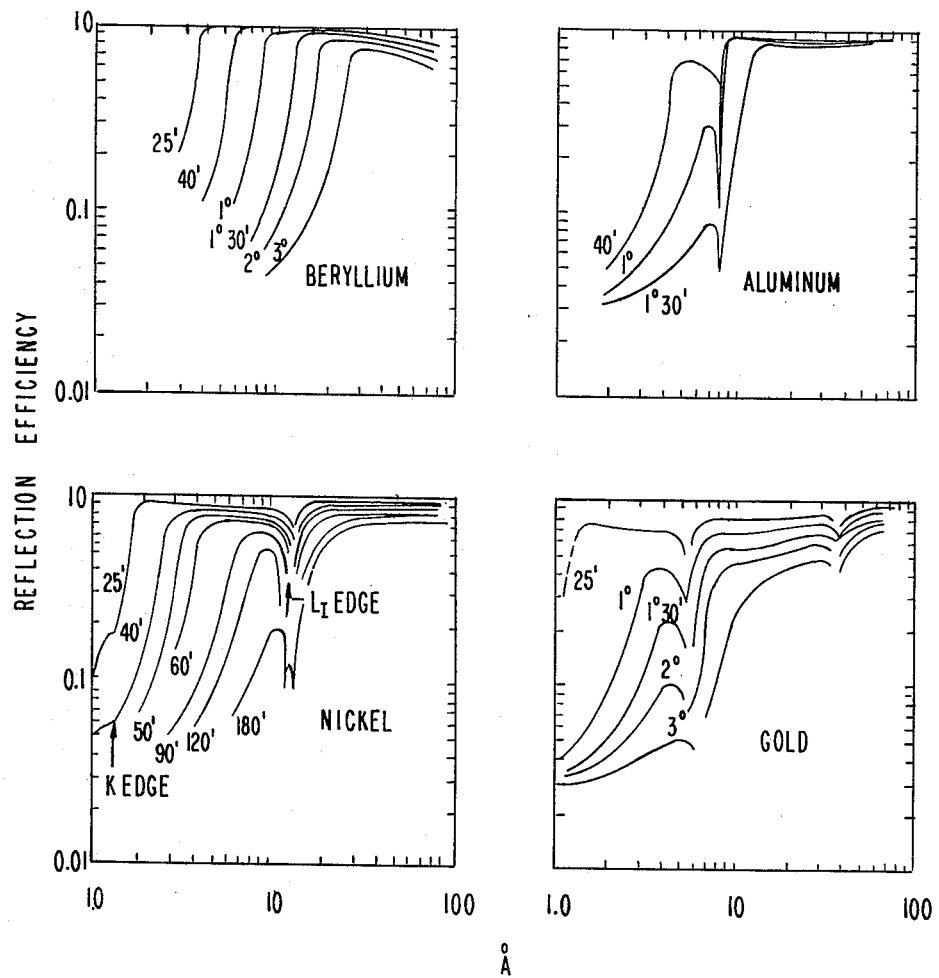

United States Patent [19]

Wang

[11] 4,317,036
[45] Feb. 23, 1982

[54] SCANNING X-RAY MICROSCOPE

[76] Inventor: Chia-Gee Wang, P.O. Box 211, Millwood, N.Y. 10546

[21] Appl. No.: 129,287

[22] Filed: Mar. 11, 1980

[51] Int. Cl.³ .................... G01N 21/24; G01N 23/20
[52] U.S. Cl. ..................................... 250/274; 250/272
[58] Field of Search ................ 250/272, 273, 274, 275

[56] References Cited

U.S. PATENT DOCUMENTS

| | | | |
|---|---|---|---|
| 2,754,425 | 7/1956 | Froemel | 250/272 |
| 3,718,817 | 2/1973 | Afanasiev et al. | 250/272 |
| 4,063,088 | 12/1977 | Dailey | 250/272 |

Primary Examiner—Alfred E. Smith
Assistant Examiner—T. N. Grigsby
Attorney, Agent, or Firm—Strimbeck, Davis & Soloway

[57] ABSTRACT

A scanning X-ray microscope including an X-ray source capable of emitting a beam of X-rays, a collimator positioned to receive the beam of X-rays and, to collimate this beam, a focusing cone means to focus the beam of X-rays, directed by the collimator, onto a focal plane, a specimen mount for supporting a specimen in the focal plane to receive the focused beam of X-rays, and X-ray beam scanning means to relatively move the specimen and the focusing cone means and collimator to scan the focused X-ray beam across the specimen, a detector disposed adjacent the specimen to detect flourescent photons emitted by the specimen upon exposure to the focused beam of X-rays to provide an electrical output representative of this detection, means for displaying and/or recording the information provided by the output from the detector, means for providing information to the recording and/or display means representative of the scan rate and position of the focused X-ray beam relative to the specimen whereby the recording and/or display means can correlate the information received to record and/or display quantitive and distributive information as to the quantity and distribution of elements detected in the specimen. Preferably there is provided an X-ray beam modulation means upstream, relative to the direction of emission of the X-ray beam, of the focusing cone means.

11 Claims, 5 Drawing Figures

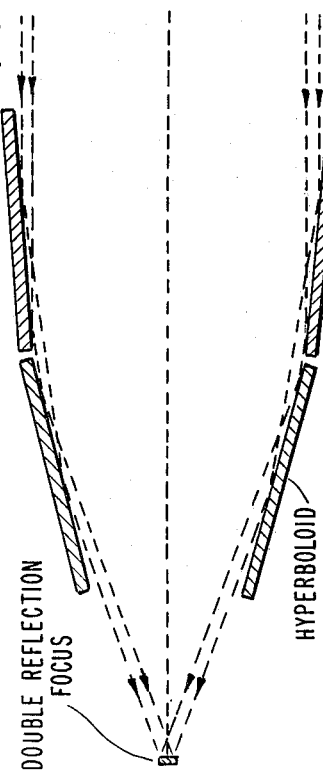
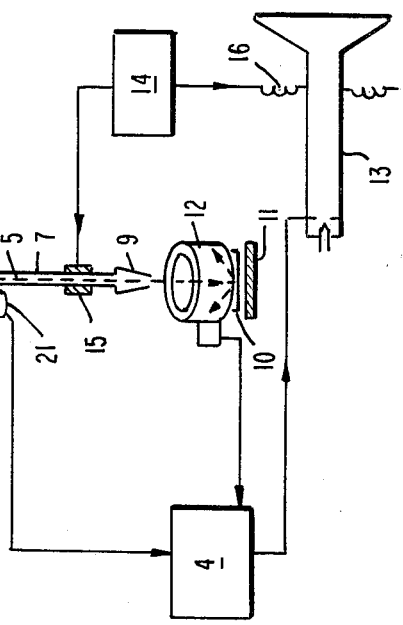
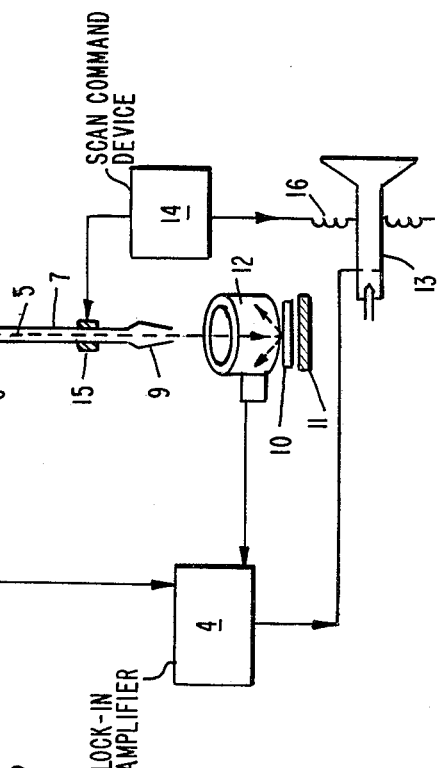

SCANNING X-RAY MICROSCOPE

BACKGROUND OF THE INVENTION

Ever since the discovery of X-ray radiation, attempts have been made to design X-ray microscopes (See "X-Ray Microscope" by Kirkpatrick and Pattee, pp 305-336, Handbuck der Physik, Volume 30, 1957.) Except for contact microradiography and the projection microscope where pencil beams of X-ray are used to project an image with little or no magnification, all X-ray microscopes with significant magnifications include systems of electron beam optics. They are in reality electron microscopes equipped with X-ray detectors. The fact that the refractive index of all known optical materials for X-ray is almost exactly unity precludes any design consideration of optical lenses. At grazing incidences, X-ray photons have been known for sometime to behave like light photons, but this knowledge was not successfully applied in any optical system until the late 1960's.

The limiting resolution of a light microscope is of the order of one-half the light wavelength, and this implies a limit of magnification to two to three thousand times. In practice, most light microscopes cannot magnify more than one thousand times. With electron microscopes, a beam of electrons is focused by electromagnetic lenses, and the wavelength of the energetic electrons are subatomic, or under one Å. The resolution of the electron microscopes is, however, not limited by the electron wavelength, but by the stability of the beam-lens interactions. With great effort to stabilize the power supplies of the lenses, the beam, and to limit the dispersion of the electron cloud where each electron in the beam carries a repulsive charge to all others and contributes to aberation, the point resolution can reach a few Å. Line resolution can generally do better than the point resolution. More recently, scanning electron microscopes (SEM) have gained great popularity. The beam spot for a typical SEM that focuses on and scans over a specimen is usually larger than 100 Å, and with synchronous motion between the scan command and the cathode ray sweep on a screen, only one electron detector is required for SEM (U.S. Pat. No. 3,191,028 by Albert V. Crewe, 1965.) Heavy elements, particularly heavy metals, have a dense electron cloud and are opaque to the electron beam. Staining with heavy metals for very thin specimen becomes a necessary step for transmission electron microscopy, while coating with heavy metals shows surface details for SEM. The use of heavy metals becomes particularly attractive when they are coated (evaporated) onto the specimen from an oblique angle. With shadows (no coating) and bright spots (heavy coating), the surface structure can be viewed in a beautiful three-dimentional perspective. A great number of techniques have been developed over the years to treat specimens with heavy metals. The fact that the heavy element under consideration is a known designated element with well defined characteristic adsorption edges is an important design consideration for a scanning X-ray microscope (SXM) or atom specific microscope ASM. A primary aim of the present invention is, with the help of certain atom specific optics, to obtain good resolution and image details. By modulating any set of X-ray bands of interest, all elements in the periodic table can be searched for, and SXM [or] ASM can also be engaged for elemental analysis, but this is not a primary aim.

When the electron detector of an electron microscope is replaced by a X-ray photon detector, the system can function as a "X-ray microanalyzer" instead of a transmission electron microscope, and can function as an X-ray microscope with scanning electron detection, X-ray detectors, on the other hand, often include a multichannel analyzer in order to distinguish one element from another and a low noise photo-detector, such as a liquid nitrogen cooled solid state detector. With a vacuum housing for the electron beam and the specimen, with electromagnetic lenses and their stable power supplier, plus various photoanalyzer equipments, the microscope becomes complex and expensive. The present invention uses only a simple system in which a beam of modulated X-rays with discriminating bands of interest for a certain designated element, focuses the beam onto a small spot, scans the beam over the specimen and displays an image without the use of a vacuum, low noise detector electronics, or a multichannel analyzer.

SUMMARY OF THE INVENTION

For any designated element in a specimen, the energy levels of its various adsorption edges are determined according to its atomic number Z and can be distinguished from any other element in the specimen. X-ray photons, with modulated bandwidth and chopped with a modulation frequency to provide, alternately, radiation with and without the distinguishing bands of the spectrum, initiate respectively a resonant adsorption inclusive, or a non-resonant scattering, with the specimen elements. A X-ray detector senses the fluorescent photon counts from the specimen and a lock-in amplifier, making use of the modulation frequency, sorts out the purely resonant counts so they may be shown as a brightness spot on a cathode ray screen. The X-ray beam is focused with grazing incidences and it scans over the specimen systematically to compose a display. Comparing to the scanning electron microscopes, ASM is very simple, has a similar resolution, and with only a small fraction of the cost.

According to the invention there is provided a scanning X-ray microscope including an X-ray source capable of emitting a beam of X-rays, a collimator positioned to receive the beam of X-rays, to collimate this beam, a focusing cone means to focus the beam of X-rays directed by the collimator onto a focal plane, a specimen mount for supporting a specimen in the focal plane to receive the focused beam of X-rays, and X-ray beam scanning means to relatively move the specimen and the focusing cone means and collimator to scan the focused X-ray beam across the specimen, a detector disposed adjacent the specimen to detect fluorescent photons emitted by the specimen upon exposure to the focused beam of X-rays to provide an electrical output representative of this detection, means for displaying and/or recording the information provided by to the output from the detector, means for providing information to the recording and/or display means representative of the scan rate and position of the focused X-ray beam relative to the specimen whereby the recording and/or display means can correlate the information received to record and/or display quantitive and distributive information as to the quantity and distribution of elements detected in the specimen.

In a prefered form of the invention there is provided an X-ray beam modulation means upstream, relative to the direction of emission of the X-ray beam, of the focusing cone means.

The invention will now be described, by way of example, with reference to the accompanying drawings, in which:

FIG. 1—is a diagrammatic cross-section of an X-ray focusing device for use in the present invention;

FIG. 2—is a diagrammatic representation of a first embodiment to the invention;

FIG. 3—is a diagrammatic representation of a modulating filter for use in a second embodiment to the invention;

FIG. 4—is a diagrammatic representation of a second embodiment of the invention utilizing the modulating filter shown in FIG. 3; and FIG. 5—is a graphical representation of the grazing reflection characteristics of berillium, nickel, aluminum and gold.

In a typical X-ray tube, a beam of electrons is accelerated by a potential bias to strike an anode target, producing X-ray photons with a spectrum having a high energy cut-off, a K-peak and/or some other peaks characteristic of the target element, and a bremsstrahlung tail at the long wavelength end. A reduction of the potential of electrical bias to the anode of the X-ray tube cuts off X-ray photons at high energy end, and a proper choice of filter material preferentially screens photons at the long wavelength end. A combination of these two measures reduces the photon spectrum to a relatively narrow bandwidth (window). Additional modulation to concentrate or deplete certain bands of interest greatly enhance the signal to noise ratio, and they are designed "up stream" in the photon path in order to simplify the detector system.

X-ray photons, particularly those near the K-edge of heavy elements, are of rather short wavelength and have a refractive index very close to unity for all optical materials. The channeling of X-ray beam therefore requires some special considerations. There are two general methods which are almost insensitive to the photon energy. One is the use of opaque diaphragms to passively block the beam passage, and the other is to bend the beam with grazing incidences where the X-ray can be reflected like light photons. By using the latter method grazing incident telescopes which can resolve celestial X-ray sources have been developed in which, using a parabolic surface followed by a hyperbolic surface, the incident X-ray beam can be focused onto a detector (U.S. Pat. No. 3,143,651 by Giacconi, Riccardo and Rossi, 1964.) Orbiting as satellites, these X-ray telescopes are providing a large amount of new astrophysical information. The double focusing cone as illustrated in FIG. 1 operates on already known principals, although a focusing cone arrangement such as is required for the present invention is significantly smaller than previously proposed and manufactured cones, which cones have been used in focusing X-ray telescopes. The focusing cones exploit the fact that X-rays behave like light-rays if they strike surfaces at a low angle. In the illustrated design and the design utilized in the present invention the X-rays are focused by first glancing of a parabolic surface and then off a hypobolic surface. It will be appreciated that in the illustration the focal length is greatly forshortened and that in the design for the present invention the total length of the conical members may be two millimeters with the focal length being 20 millimeters.

The focusing cone is composed of paraboloid followed by hyperboloid. Let x be the optical axis, with $x=0$ be measured from the intersection of the two conical surfaces, and r is the radical dimension from the optical axis.

For a paraboloid, $r^2 = 4p(x+p+c+k)$, and for a hyperboloid, $$\frac{(x+k)^2}{h^2} - \frac{r^2}{c^2 - h^2} = 1$$

with $2c+F=K+c=$ focal distance of the paraboloid, $F=$ focal distance of the system, $p=$ the tip of the paraboloid to its focal point, and h is adjusted to match the two surfaces at $x=0$. The constants p,c,k, and h can be expressed by the focal length F, radius of the focusing surface $r_o$ at $X=0$, the projected length (on the x axis) of each surface L. with $r_o-1.5$ mm, in unit of mm, the two surfaces can be approximated as follows:

$$r^2 = 0.00132196(x+2.51797)$$

for the paraboloid, and $$2.6881(x+1.9074)^2 - 2637.6r^2 = 1$$

for the hyperboloid.

From a two-surface focusing cone, besides the focused rays reaching the focusing point, there can also be the direct and singly reflected rays accidentally reaching the specimen. The latter can be blocked, in an astronomical telescope, by simply placing an aperture on the optical axis. For the ASM, however, the photon-detector and the specimen is large compared to the beam spot and there is no room to place such and aperature. However the key concern is not that of having stray rays reaching the beam spot; the rays were modulated upstream and all X-ray photons reaching the designed beam spot are equally useful. The problem for ASM is that the stray rays cutting the specimen outside of the designated area would effectively enlarge the beam spot. In order to cause more focused rays to reach the beam spot, we can use relatively long focusing cones, that is, with $L-10$ to 20 $r_o$ instead of $L=2r_o$ as in the telescope.

Consider a X-ray photon interacting with a specimen coated with the designated heavy element. If the photon energy is just above an "A" absorption edge of the element ("A" can be K, L, M, or any one of the electron shells) the probability is rather high that the photon will create an A-ionization and a subsequent A-fluorescent emission. If the photon is below the A-edge, there will not be a resonant scattering leading to the A-ionization. The probability of non-resonant scattering with other elements in the specimen, being very far away from the respective absorption edges, remains virtually the same whether the photon is above or below the A-edge. In a first embodiment of ASM, the potential bias of the X-ray tube is set alternately at slightly above or below the designated A-edge. The frequency of modulation for the bias is used as a chopping signal to be sensed by a lock-in amplifier which sorts out the difference of the count between those fluorescent events at above and those at below the A-edge bias. This difference of counting is a quantitative indication of the designated element covered by the focused beam spot, and is sequentially displayed as brightness at a corresponding spot on a cathode ray screen. Systematically, the beam spot is moved relative to the specimen to cover certain desired region of the specimen, and a picture is thus assembled on the cathode ray screen.

The first embodiment as illustrated in FIG. 2 comprises an X-ray generator 1, the power supply for which is produced by a electrical bias for the the anode produced by a power supply 2 which produces a steady supply to be modulated by a modulator 3 before being used to bias the annode of the X-ray generator 1. The modulator 3 modulates the steady power supply to produce a square wave electrical supply the upper potential of which determines the high energy cutoff of the X-rays generated by the X-ray tube, just above the K-peak or another peak characteristic of the designated element, while the lower potential of the square wave will cause the X-ray generator 1 to produce X-rays the high energy cut-off of which will be slightly below the selected peaks or peaks of the target element. The modulator 3, produces the modulation of the anode bias at a desired frequency and provides an output signal to a lock-in amplifier 4, to provide information which is definitive of the frequency of modulation.

The X-ray beam 5 emitted by the generator 1 first passes through a filter 6 which preferentially screens photons at the long wave length end of the X-ray spectrum. The filtered beam is then directed into collimator 7 by means of a concentrating cone 8 defined by a straight conical wall the included angle of which is approximately 1° to 2° and the outlet area of which is approximately 1 square millimeter. The collimator, which is approximately 1 to 2 centimeters long has a straight internal bore of approximately 1 square millimeter with an internal surface smoothness of 10 Å or less. The concentrating cone 8 has a similar smoothness. The collimator 7 may be drawn pipetting glass which will not require an internal coating if the glass is a lead glass.

The end of the collimator 7 remote from the concentrating cone 8 is a focusing cone 9 which has an axial length of approximately 2 millimeters and an outlet area of approximately 1 square millimeter. The focusing cone 9 is aligned axially with the collimator 7 and concentrating cone 8 to focus the X-ray beam with a focal length of approximately 10 millimeters.

The specimen 10 is disposed in or adjacent the focal point of the X-ray beam and is carried by a mount 11. Adjacent or surrounding the specimen, with a window or windows for passage of the X-ray beam, is a scintillation detector 12 to detect flourescent emissions of the target element in response to the focused X-ray beam. The output from the scintillation counter 12 is fed to lock in amplifier 4 which by utilizing the information concerning the modulation of the bias signal received from the modulator 3 differentiates between the signal from the scintillation detection when the X-ray beam includes energy at the selected peak or peaks and the periods when it does not include such energy, as is determined by the high and low energy levels of the modulated anode bias. This differential signal produced by the lock-in amplifier 4 is fed to the electron gun of a cathode ray tube 13.

The scanning aspect of the first embodiment of the invention is provided by a scan command device 14 which controls a scanning movement of the X-ray beam 5 by way of a scan control 15. The scan control 15 is preferably a mechanical cam operated arrangement which cooperates with the collimator 7 to bend the collimator 7 sufficiently to cause the X-ray beam to scan in a desired manner over the surface of the specimen 10. Alternatively, the scan control might be electro-magnetic in nature with the electro-magnetic force utilized to bend the collimator. Further, the collimator may be pivoted about axes adjacent the concentrating cone 8 rather than being bent. The extent of the scanning movement is of an order which will change the angle of the X-ray beam under 2°. The scan may be of a continuous nature or may be of a stepped nature with the X-ray beam being sequentially directed at discrete points on the specimen and held steady thereon for a discrete reading. At each point the scan command device 14 also supplies a scan control signal to the scanning coils 16 of the cathode ray tube 13, such that the electron beam of the cathode ray tube is caused to scan in synchronism with the scanning of the X-ray beam by the scan control 15.

The focusing cone and the elongate tubular collimator are attached together such that they move in unison under the control of the scan control and scan command device.

It will be appreciated that the scanning may alternatively be achieved by moving the specimen relative to the X-ray beam and that this may be achieved in a similar manner and by a similar mechanism to the scanning arrangement described above.

Typically, the specimen will have an area of approximately 1 square millimeter, the depth of focus of the X-ray beam is approximately ½ to 1 millimeter, resolution of 200 Å is possible with the sequential scanning of the sample in a stepped manner to sequentially expose 100 discrete areas per scan across the sample with the desired area of the sample being in totality exposed to 100 scans to cover its surface. The image generated on the cathode ray tube would in this instance be a representation of the 10,000 individual readings taken, each scan line requiring approximately 10 seconds to complete. Changes in resolution may be achieved, where less resolution in the highest possible resolution is 0 desired, by moving the sample toward or away from the X-ray tube relative to the focal plane.

As indicated in FIG. 2, the optical path of ASM starts with a X-ray beam already modulated with desired energy bands and modulation frequency, and the photodetector in such a design can therefore be rather simple. It needs only to count the fluorescent photons from the specimen without regard to the beam energy, position, the specimen geometry, or the energy of the fluorescent X-ray events. This freedom of detector choice eliminates the need to use low noise detectors cooled with liquid nitrogen or the use of a multichannel analyzer. A simple scintillating shell surrounding the specimen, as employed in the first embodiment where X-ray photons are converted into light, to be sensed by a photo-multiplier for signal, will suffice.

In order to make use of more energy bands of interest so that there are more X-ray photons to interact with the designated element in the specimen, a second embodiment to produce the modulated X-ray will now be described. The first embodiment is more suited to a designated heavy element where the energy bands of interest are far away from the rest of the elements in the specimen, while the second embodiment takes into consideration that when the useful energy band for discriminating scattering is near that of other elements and therefore narrow and limited; one must make use of more than one energy band if possible, and at the same time filter away some of the background bands that are anticipated from the specimen. In the first embodiment, modulation of X-rays at the high energy end was provided by the modulated bias of the power supply, while in the second embodiment, a modulating filter is used instead. The filter is placed at near the beginning of the optical path, and it provides the modulated energy bands as well as the modulation frequency.

The modulation filter is a simple spinning disc, one-half of which contains the designated element of the specimen and the other one-half free of such element.

As shown in the FIG. 3 the modulator disc 17 is divided into two equal halves, one comprising the background material 18 and the other 19 comprising the background material and the element to be detected. The disc is large relative to the beam size which is diagramatically shown at 20, which beam is arranged in the second embodiment to pass through the disc adjacent the periphery thereof. It will be appreciated that although the disc is shown divided into two equal halves, the arrangement of the portions 18 and 19 is not restricted to such an arrangement, the only requirement being that the beam be caused alternately to pass through areas comprising the background material and the element to be detected in a predictable manner.

The part of filter containing the designated element absorbs the bands of interest in the X-ray spectrum so that there will be no resonant scattering with such element in the specimen, while the other half of the filter, missing the designated element, is transparent to those bands of interest in the spectrum and will give rise to the distinguished scattering for the designated element in the specimen. The difference of the two cases caused by the modulating filter is sorted out by a lock-in amplifier which is synchronized to the modulating frequency. This difference represents quantitatively the designated element in the specimen covered by the X-ray beam, and is displayed as a spot of brightness on a cathode ray screen. Consider an example of the aluminum bridge network evaporated on silicon. With an atomic number of 13 for Al and 14 for Si, these elements have very similar energy levels. The K-edge for Al is 1.56 KeV (7.95 Å) and for Si is 1.84 KeV (6.74 Å). By setting the power supply of the X-ray tube at 1.80 KeV, we can rest assured that the K-band of Si would not be excited. The modulating filter can be made of silicon with one-half of it coated with aluminum (Al-on) and the other half without aluminum (Al-off). During the Al-on half cycle, aluminum bands of the X-ray spectrum are virtually depleted and therefore no fluorescent event of Al from the specimen is emitted, while during the Al-off half cycle, aluminum bands can pass through the filter and excite resonant scattering of Al from the specimen. Element Si would contribute the most background counts, and the fact that the filter is composed of silicon, it has a substantial effect on the reduction of silicon counts from the specimen.

The resolution of an electron microscope can be a few Å. For SEM, however, the beam spot is usually greater than 100 Å. There are two main reasons for using relatively large beam spot. One is of course the nature of the specimens where a better resolution may not be necessary, the other reason is the scanning time required. By reducing the beam spot by a factor of $10^2$, the scanning time must be increased by $10^4$ in order to cover the same sample area. For a typical scan with $10^3$ seconds, a time increase of $10^4$ would imply a scanning time of one-third of a year! Being able to adjust the size of the beam spot is therefore highly desirable so that a fine beam (small spot) needs only be applied selectively to the most interesting region. With ASM, X-ray beam is focused by way of converging the X-rays from a focusing tube, and size of the beam spot can easily be arranged as a function of the focal distance and therefore as part of the scan variables.

The second embodiment to the invention as shown in FIG. 4 will now be described. In FIG. 4 components which are similar or identical to those used in the first embodiment are given the same reference numerals as used with respect to the first embodiment. These components will not be described again unless they differ in some significant manner with respect to the invention, from the components already described with respect to the first embodiment. In this second embodiment the power supply is not itself modulated and supplies a steady anode biasing current to the X-ray tube in order that the X-ray tube produce X-rays having a high energy cut-off just above the K-peak or another peak characteristic of the designated element. X-rays emitted by the X-ray tube are passed through concentrating cone 8 which in this second embodiment is separated from the collimator 7 by the modulating disc 17 through which the X-ray beam from the concentrating cone must pass to the collimator 7. The modulation disc 17 is rotated about its axis by a motor 21 at a desired rate to provide a modulation of the X-ray beam in order that the X-ray beam be modulated by the alternate exposure of the background material areas and the areas comprising background material and the target element. Motor 21 includes sensor which will provide an output signal representing the modulation frequency and characteristics and this output signal is fed to the lock-in amplifier 4 in place of the modulation information signal which in the first embodiment was provided by modulator 3. Apart from the different manner of achieving modulation in the second embodiment the operation of the construction of the second embodiment is similar to that of the first embodiment.

In both embodiments it will be appreciated that all regulation and control of the X-ray energy is carried out prior to the focusing and scanning of the beam with the consequence that the apparatus can be relatively simple.

Now to consider the channeling of photons into a small focus, and to give particular attention to the possibility that the beam can be aligned very inexpensively. The K-edge wavelength of X-ray photons of heavy elements are subatomic, or under one Å. Therefore, similar to electron microscopy, the limiting resolution of X-ray microscopy can be of atomic dimension. Kirkpatrick in 1948 devised a first X-ray microscope with a concave spherical mirror for grazing incidence and was able to resolve points separated by 70 Å. The X-ray telescope program developed by Giacconi's group (NASA CR 717, 1967, or N67, 18160 from the National Technical Information Service, Springfield, Va. 22161) gave a resolution of a few arc seconds. If the telescope can be scaled down by about two orders of magnitude, a beam piped down at 1 mm in width can be focused onto a spot at $1-2 \times 10^2$ Å.

There are two considerations that require clarification for the design of focusing cones. One point is that reflecting surface may not need a smoothness up to an atomic dimension. Viewed from a photon travelling down with a grazing angle $\theta$, the atomic spacing d of the surface material becomes $d \sin \theta \sim d\theta$ which is small relative to d when $\theta$ is only a degree or so. The second point is the choice of proper metal to coat the surface. Light elements have fewer electrons and therefore fewer photon-traps to absorb the incident photons. The scattering cross-section of X-ray photons depends more sensitively, however, on the unfilled electron states. Take beryllium for example. The element Be is heavier than Au and reflects less efficiently than gold at short wavelengths, yet a beryllium surface is more efficient than gold at longer wavelengths. The performance of a reflective system at certain wavelengths is also strongly effected by the absorption edges nearby. In fact, this "strong effect", or the change of scattering characteristics, is important to this invention and care is required as to its function on the reflective material. FIG. 5 is the theoretical efficiency of grazing reflections calculated from Fresnel's equation for four materials Al, Ni, Au, and Be. The values were from American Science and Engineering, Inc. and they agree with experimental data very well.

The beam size of a X-ray tube output is relatively large, and it needs to be concentrated into a size of a mm or so, piping down towards the specimen with a lead glass pipetting tube or with a hypodermic needle, and focused again to a desired dimension. The focusing cone can be formed by a variety of processes. Due to the smallness of dimension, there will be no gravitational distortion and deformable material such as plexiglass can readily be used. The cone is first coated with certain metal and formed into shape by molding from its inner surface, or be deformed from the outer surface. The contour of focusing surface resembles closely that of a straight cone with a slope from the optical axis of a degree or two. Starting from a straight tube or cone, a slight heat expansion or pressure differential would suffice to force the plexiglass into a desired contour. A mold or mandrel for the inner contour is preferred. Under photographic reduction using an electron microscope, a surface accuracy can be etched upon or sputtered off to an accuracy of an atomic dimension. Once a mandrel is made, it can produce focusing cones with minimal cost. The focusing cones are heat relieved and housed in a cast for proper handling. The mathematical formulation of the reflecting surface shown in FIG. 1 is known to an exact accuracy and can be programmed and drawn for photographic reduction without deviation, therefore the smoothness of the mandrel is a major source of concern on the efficiency of reflectivity.

Some optical parameters the of focusing cone are designed as follows: from a width of 1 mm of the piping tube, the beam reaches the two-surface focusing cone and is concentrated into a spot of 200 Å at a focal distance of 10 mm with a depth of field 1 mm. The depth-of-field is extremely large due to the slow-convergent nature of grazing reflections. The second reflective surface, a hyperboloidal cone, can be approximated by a straight cone with a slope to the optical axis at 2 and the size of the focal spot can be altered by simply changing the focal distance. Due to the very large depth-of-field, a slight bending of the piping tube and therefore slightly altering the focusing distance as the focusing cone is fitted at the end of the pipting tube, would not move the X-ray beam out of fucus. ASM is a scanning microscope with sequential illumination, and the command of the sequence of illumination can simply be delivered to the piping tube by slightly bending it.

Next we consider the production of modulated X-ray photons. The modulation involves the energy bands of interest in the X-ray spectrum as well as the modulation frequency. Some recent experiments on the X-ray channeling radiation from positrons and relativistic electrons (Phys. Rev. Letters 42, 1148 and 43, 1723, both of 1979) may provide a new source of tunable X-ray photons that can be focused through certain axis of a crystal lattice, but they require far more complicated equipment than is considered in this disclosure. In the first embodiment, more suitable for a heavy designated element where the bands of interest is far away from that of the rest of the elements in a specimen, high density of photons can be created through a relatively wide energy window to interact with the designated element of the specimen. Modulation for the power supply bias is electronically programmed and no limit need be placed on the modulation frequency. With a sufficent signal from the lock-in amplifier, the sequential illumination can be achieved very quickly and the scanning time to compose an image picture thereby reduced. In the second embodiment, the designated element has a atomic number very near that of the rest of the element in the specimen, such as aluminum in a background of silicon, or phosphorus in a biological tissue. More than one band of interest will be utilized if possible, and some of the anticipated bands of noise be eliminated from X-ray spectrum. A silicon disc as the modulation filter with one-half coated with aluminum in order to resolve the aluminum bridge network in a microelectronic chip has been described. In a similar manner, with phosphorus as the designated element in a tissue specimen. P is the heaviest element in the DNA and has A K-edge of 2.1435 KeV (5.78 Å). The filter material can simply be a bag of water in the form of a disc one-half of which contains phosphoric acid. During the P-acid-on half cycle, the phosphoric bands will be deleted and there will not be P-fluorescence in the specimen, while during the P-acid-off half cycle, the phosphoric bands interact preferentially with the element P in the specimen and provide the necessary signal for the lock-in amplifier. For the human DNA double helix, there are over three billion P-contained units in each cell nucleus. Clearly, being able to resolve them, map out their morphology during various cell cycles without staining of any kind, would be of utmost interest in biology.

Next we consider a more traditional example of electron microscopy in biology $OsO_4$ has been extensively employed to stain tissues and cellular components because of its unique properties of opacity to the electron beam, high density, amorphous character, and insolubility. It is particularly useful in the study of enzymatic activities. The $L_I$-edge of osmium is 12.972 KeV (0.956 A), and in the first embodiment, the high energy cutoff of the X-ray power supply can be set at $12972 \pm 30$ Volts. The modulating $\pm 30$ Volts is sent with a modulation frequency which is also sensed by the lock-in amplifier. During the $L_I$-on bias (12972+30 Volts), the photo-detector will sense all fluorescent X-ray photons including the $L_I$ series of osmium, while during the $L_I$-off bias (12972−30 Volts), the photo-detector will not sense the $L_I$ lines of osmium from the specimen. The difference of the two cases represents the amount of osmium covered by the X-ray beam and is delivered as an output of the lock-in amplifier. If very soft X-ray photons are considered instead, one can use the $N_I$-edge of Os at 654 Volts (18.96 Å) and apply a modulating bias of $\pm 10$ Volts. Use of $OsO_4$ as a filter material outlined in the second embodiment will probably give better signal to noise ratio, and the filter can contain some typical tissue elements in order to reduce the background fluorescent events. In the second embodiment of ASM, the modulation frequency is nothing but the rotation of the filter disc, and unless the disc and the driving motor is specially designed, the frequency value is somewhat limited. Note also that for photons with wavelength longer than 10 Å, the usual type of scintillators become inefficient and photoelectric detectors such as CsI, which is very efficient in its delivery photoelectrons for soft X-rays, can be used as photocathodes for electron multipliers. Being able to deal with relatively soft X-rays, metals such as Al, Ni, Fe, etc., that are normally considered too light for electron microscopy, can also be used, in either embodiment of ASM.

In a series of five symposiums (International Congress on X-ray Optics and Microanalysis, 1956, 1959, 1962, 1965, and 1968), a great deal of possibilities for the use of X-ray microscopy were raised, including biological research, clinical services, metallurgy, etc.

Another major use is in the development and production of microelectronic circuits. There are four basic atomic elements that need be added on to a silicon wafer in order to form various components of the circuit. For n-type semiconductors where electrons are the main current carrier, phosphorus or another pentavalent elements is required to dope or displace a silicon atom in the silicon crystal lattice in order to have an extra electron in the crystal structure. For p-type material where holes are the main carrier, boron or other trivalent elements is doped. Metals such as aluminum is evaporated upon to form electric contact or the bridge network as well as the plate for capacitors. Oxygen, the last of the four elements, is used to form $SiO_2$, a very good insulator. Being able to resolve elements such as P or Al in a background of Si and map out their concentration is certainly of great interest to the industry. When the seqential illumination of ASM is projected from several different angles and with the help of some data processing, a three dimensional structure may be reconstructed and displayed. The fact that ASM is non-intrusive to the specimen and does not require a vacuum environment, means the examination can be part of the manufacturing process. A more straightforward application in quality control is simply the monitoring of dust particles. Consider a metal mask without carbon for example. Any carbon containing dust particle appearing on the metal mask trigger a carbon-K-scanner where a beam of 300 eV photons is monitoring above its K-edge of 284 Volts (43.68 Å). A beam of this kind need not even be focused. Note that if the K-series photons of Al is too soft to leave the chip, we may need to replace Al with Cu or Ag where their K-photons are of much harder X-ray and thereby of greater penetrative power. Another area of application is that of photoengraving or lithography. The dramatic cost reduction in microelectronic circuit during the past two decades achieved not from major new breakthrough in fabrication technology, but by the increased size of wafer, reduction of size of circuit elements and their connection, and gradual elimination of defects in various manufacturing steps. Although electron beam lithography has performed great services, with substantial cost reduction in ASM as well as some new features that no existing microscope can provide, this disclosure can be another one of the evolutionaly steps for the industry. Note that the dramatic increase in circuit density has yet a long way to develop before it meets a physical limit. Take a biological bit of information for example. An elementary nerve signal requires about $10^3$ atoms to form, and in a space of 1 $mm^3$, one should be able to pack, if one can be as clever as nature, about $10^{18}$ bits of information. Since the introduction of planar transistor in 1959, the complexity, or number of elements in a microelectronic circuit, has been doubled every year, reaching a current level of $2^{20}$ elements ($10^6$), which is indeed impressive but still a long way from $10^{18}$. The limiting element to achieve more arises from two areas. One is the dimension of the circuit elements such as the conduction bridge which has a current dimension of about one micron; of the same order of the light wavelength. More extensive use of electron beam or X-ray lithography should certainly help in this direction. The other limiting area is the economics of yield. Packing more elements than doubling each year apparently exceeds the learning ability and gives negative returns. Price of the product is another important incentive for research and development. The same product declines in constant dollar by about 25% each year. Any company in this business falling behind other competing companies by a year suffers a price disadvantage of 25%, conversely, being ahead of others by a year also earns a cost advantage of 25%. Needless to say, useful new tools are of fierce interest to the industry, and if ASM can be developed there, the benefit may be shared with biomedical fields as well.

I claim:

1. A scanning X-ray microscope including an X-ray source capable of emitting a beam of X-rays, a collimator positioned to receive the beam of X-rays, to collimate this beam, a focusing cone means to focus the beam of X-rays, directed by the collimator, onto a focal plane, a specimen mount for supporting a specimen in the focal plane to receive the focused beam of X-rays, an X-ray beam scanning means to relatively move the specimen and the focusing cone means and collimator to scan the focused X-ray beam across the specimen, a detector disposed adjacent the specimen to detect emmissions by the specimen upon exposure to the focused beam of X-rays to provide an electrical output representative of this detection, means for displaying and/or recording the information provided by the output from the detector, means for providing information to the recording and/or display means representative of the scan rate and position of the focused X-ray beam relative to the specimen whereby the recording and/or display means can correlate the information received to record and/or display quantitative and distributive information as to the quantity and distribution of elements detected in the specimen.

2. A scanning X-ray microscope according to claim 1, comprising X-ray beam modulation means upstream, relative to the direction of emission of the X-ray beam, of the focusing cone means.

3. A scanning X-ray microscope according to claim 2, wherein the modulation means is disposed upstream of the collimator.

4. A scanning X-ray microscope according to claim 2, wherein the modulation means modulates the X-ray beam to provide an alternating energy level which is alternately above and below one or more characteristic peaks of responsiveness to X-rays of a desired target element.

5. A scanning X-ray microscope according to claim 4, wherein the modulation means is a modulator for the anode biasing electrical supply of the X-ray generator and this modulator modulates that supply to provide a square wave the respective high levels and low levels of which provide the desired modulation of the X-ray beam.

6. A scanning X-ray microscope according to claim 4, wherein the modulation means is a modulator filter disposed between the X-ray source and the focusing cone means, the modulator filter consisting of a least a first area consisting of a filter material which will filter unwanted frequencies from the X-ray generated by the X-ray source and a second discrete area consisting of a material which will filter said unwanted frequencies and the frequency of X-rays required to excite the desired peak or peaks of the target element.

7. A scanning X-ray microscope according to claim 2, wherein a lock-in amplifier receives the information produced by the detector and modulation information from the modulator and compares these to determine the difference between signals from the detector when the specimen is exposed to the different levels of modulation of the X-ray beam, the lock-in amplifier providing an output to the record and/or display means representing the difference between the signals produced by the detector with the different levels of modulation.

8. A scanning X-ray microscope according to claim 1, wherein the record and/or display means is a cathode ray tube display device.

9. A scanning X-ray microscope according to claim 1, wherein the detector is a scintillation detector.

10. A scanning X-ray microscope according to claim 1, wherein the X-ray beam scanning means deflects the collimator and focusing cone means to scan the beam across a specimen.

11. A scanning X-ray microscope according to claim 10 wherein the X-ray beam scanning means scans the beam in a step-by-step manner sequentially exposing discrete areas of the specimen to the focused X-ray beam for discrete periods of time.

* * * * *